United States Patent
Elghazzawi

(12) 
(10) Patent No.: US 6,574,491 B2
(45) Date of Patent: Jun. 3, 2003

(54) METHOD AND APPARATUS FOR DETECTING A PHYSIOLOGICAL PARAMETER

(75) Inventor: Ziad F. Elghazzawi, Newton, MA (US)

(73) Assignee: Siemens Medical Systems Inc., Iselin, NJ (US)

( * ) Notice: Subject to any disclaimer, the term of this patent is extended or adjusted under 35 U.S.C. 154(b) by 99 days.

(21) Appl. No.: 09/777,546

(22) Filed: Feb. 6, 2001

(65) Prior Publication Data

US 2002/0007114 A1 Jan. 17, 2002

Related U.S. Application Data

(60) Provisional application No. 60/181,482, filed on Feb. 10, 2000.

(51) Int. Cl.$^7$ ................................................. A61B 5/00
(52) U.S. Cl. ......................... 600/323; 600/324; 600/336
(58) Field of Search ............................... 600/322–326, 600/330, 336

(56) References Cited

U.S. PATENT DOCUMENTS

| | | | |
|---|---|---|---|
| 4,955,379 A | 9/1990 | Hall | |
| RE33,643 E | 7/1991 | Isaacson et al. | |
| 5,246,002 A | 9/1993 | Prosser | |
| 5,662,105 A | 9/1997 | Tien | |
| 5,807,247 A | * 9/1998 | Merchant et al. | ............ 600/310 |
| 5,807,267 A | * 9/1998 | Bryars et al. | ............... 600/500 |
| 5,846,190 A | 12/1998 | Woehrle | |
| 5,885,213 A | 3/1999 | Richardson et al. | |
| 5,891,025 A | * 4/1999 | Buschmann et al. | ......... 600/331 |
| 5,924,980 A | 7/1999 | Coetzee | |
| 5,934,277 A | 8/1999 | Mortz | |
| 5,971,930 A | 10/1999 | Elghazzawi | |
| 5,995,859 A | 11/1999 | Takahashi | |
| 6,036,642 A | 3/2000 | Diab et al. | |
| 6,094,592 A | 7/2000 | Yorkey et al. | |
| 6,122,535 A | 9/2000 | Kaestle et al. | |
| 6,393,311 B1 | * 5/2002 | Edgar, Jr. et al. | ........... 600/323 |

* cited by examiner

Primary Examiner—Eric F. Winakur
Assistant Examiner—Matthew Kremer
(74) Attorney, Agent, or Firm—Alexander J. Burke

(57) ABSTRACT

A system for detecting a physiological parameter from a physiological signal, includes a source of the physiological signal. Circuitry, coupled to the signal source, detects spectral peaks in the physiological signal. Calculating circuitry, coupled to the spectral peak detecting circuitry, calculates a parameter value corresponding to each detected spectral peak. Weighting circuitry, coupled to the calculating circuitry and the spectral peak detecting circuit, assigns a weight to each peak according to a feature of a signal and the parameter value corresponding to that peak. Circuitry, coupled to the weighting circuitry, selects the peak according to a predetermined criterion. Output circuitry, coupled to the selecting circuitry and the calculating circuitry, then generates the parameter value corresponding to the selected peak.

39 Claims, 2 Drawing Sheets

METHOD AND APPARATUS FOR DETECTING A PHYSIOLOGICAL PARAMETER

CROSS REFERENCE TO RELATED APPLICATIONS

This application expressly claims the benefit of earlier filing date and right of priority from the following co-pending patent application, which is assigned to the assignee of the present invention and have the same inventor: U.S. Provisional Application Serial No. 60/181,482, filed on Feb. 10, 2000, entitled "METHOD AND APPARATUS FOR DETECTING A PHYSIOLOGICAL PARAMETER." The above cited patent application is expressly incorporated in its entirety by reference.

FIELD OF THE INVENTION

The present invention relates to detecting a desired physiological parameter from physiological electrical signals, and more particularly to removing artifacts from the physiological signal in order to more accurately detect the desired parameter.

BACKGROUND OF THE INVENTION

It is often required to detect a physiological parameter from electrical physiological signals. For example, parameters related to the functioning of the heart are detected using known electrocardiogram systems; parameters related to the functioning of the brain are detected using known electroencephalogram systems, and the parameters of blood oxygen concentration and pulse rate are detected using known oximeter systems. In the remainder of this application, pulse oximeter systems will be described in more detail, though one skilled in the art will understand that the systems, circuits, and methods in the description may be modified to apply to other systems which detect physiological parameters from electrical physiological signals.

Known oximeter systems use light signals to detect the blood oxygen concentration. Light of two different wavelengths is made incident on blood perfused flesh, and either transmitted or reflected light is detected, converted to an electrical physiological signal, and that electrical signal processed to detect the physiological parameter of blood oxygen concentration, all in a known manner. It is well known that many factors introduce noise into the electrical signal: for example patient movement, changes in ambient light level, and, to a lesser extent, EMI from power wiring and/or other operating electrical equipment in the vicinity of the oximeter system.

In order to enhance accuracy, much work has been done to detect accurately the electrical oximetry signals in the noise inherent in such systems. Some prior art systems transform the time domain electrical physiological signal (including noise) into the frequency domain, and perform further processing in the frequency domain. Such systems use a Fourier transform to transform the electrical physiological signal into the frequency domain. More specifically, a discrete Fourier transform of some form, preferably a fast Fourier transform (FFT) is used. The frequency domain signals are then analyzed to separate the physiological signal from the noise and detect the desired parameter.

U.S. Pat. No. 6,122,535, issued Sep. 19, 2000 to Kaestle et al., illustrates a system in which FFTs are calculated of both the IR and red light representative signals generated by the oxymetric sensor. From the FFTs a magnitude transform is calculated for both the red and IR signals. The magnitude transform for one of the signals is plotted on the x axis against the magnitude transform for the other of the two signals on the y axis. The resulting x-y plot includes what are termed needles extending radially away from the origin. The magnitude and angle of these needles, and other parameters related to them, are compiled in a table. Each entry in the table is scored according to various criteria. The entry with the highest score is selected as representing the actual pulse rate of the patient. Data from the FFT related to this entry is then processed to generate pulse rate and blood oxygen concentration ($SpO_2$) parameters.

U.S. Pat. No. 6,094,592, issued Jul. 25, 2000 to Yorkey et al. illustrates another system in which FFTs are calculated on both the IR and red light representative signals generated by the oxmetric sensor. An $SpO_2$ parameter is calculated for each and every point in the FFT. A histogram is then constructed of all the $SpO_2$ parameters previously calculated. One of the $SpO_2$ parameters is selected from the histogram information according to a set of rules. This $SpO_2$ value is displayed as the blood oxygen concentration parameter.

U.S. Pat. No. 5,924,980, issued Jul. 20 1999 to Coetzee, illustrates yet another system in which FFTs are calculated on both the IR and red light representative signals generated by the oxymetric sensor. In this patent, "good" and "bad" portions of the light representative signals generated by the oxymetric sensor are identified by comparing the light representative signals to an "ideal" waveform. Outliers are identified and deleted by correlating the red and IR light representative signals. As a result of the correlation the adverse effect of the noise signals is minimized, and the $SpO_2$ value is calculated in a more accurate manner.

All of these prior art system require a substantial amount of processing, and consequently a substantial amount of power. A system which requires less processing and consumes less power is desirable.

BRIEF SUMMARY OF THE INVENTION

In accordance with principles of the present invention, a system for detecting a physiological parameter from a physiological signal, includes a source of the physiological signal. Circuitry, coupled to the signal source, detects spectral peaks in the physiological signal. Calculating circuitry, coupled to the spectral peak detecting circuitry, calculates a parameter value corresponding to each detected spectral peak. Weighting circuitry coupled to the calculating circuitry and the spectral peak detecting circuit, assigns a weight to each peak according to a feature of a signal and the parameter value corresponding to that peak. Circuitry, coupled to the weighting circuitry, selects the peak according to a predetermined criterion. Output circuitry, coupled to the selecting circuitry and the calculating circuitry, then generates the parameter value corresponding to the selected peak.

DETAILED DESCRIPTION OF THE INVENTION

Figure 1:
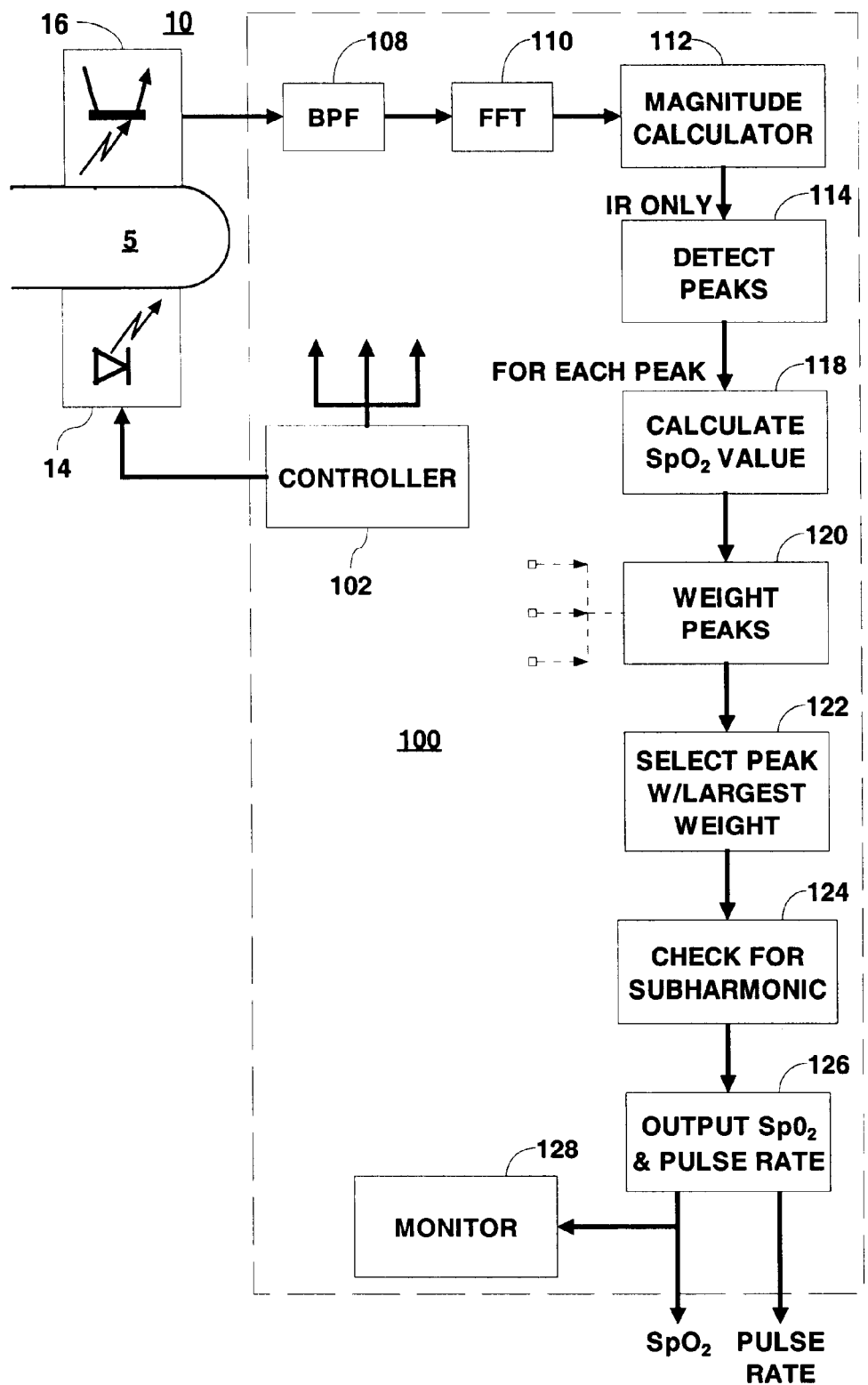
FIG. 1 is a block diagram illustrating a blood oxygen concentration ($SpO_2$) detection system according to principles of the present invention.

FIG. 1 is a block diagram representing the blood oxygen concentration ($SpO_2$) detection system according to principles of the present invention. In FIG. 1 in oxymetric sensor 10, represented by the combination of a light source 14 and a light sensor 16, is connected to a control circuit 100. In FIG. 1 an output terminal of a controller 102 is coupled to an input terminal of a light source 14. Additional output terminals of controller 102 are coupled to respective control input terminals (not shown) of other circuitry within the control circuit 100. One skilled in the art will understand what control signals are required, how to generate them, and how to interconnect them with the circuitry within the control circuit 100 requiring them.

The light source 14 is configured to emit light incident on blood perfused flesh 5, such as a finger or ear lobe, as is known. The light transmitted through, or reflected from, the flesh 5 is received by a light sensor 16. An output terminal of light sensor 16 is coupled to a serial connection of a band pass filter (BPF) 108, an FFT calculating circuit 110, a magnitude calculator 112, a peak detector 114, an $SpO_2$ value calculator 118, a peak weighting circuit 120, peak selection circuitry 122, subharmonic checking circuitry 124, and circuitry 126 which produces output signals representing the $SpO_2$ and pulse rate parameters. A first output terminal of the output circuit 126, generates the $SpO_2$ parameter value and is further coupled with input terminal of a monitor 128. A second output terminal of the output circuit 126 produces a pulse rate representative signal.

In operation, the light source 14 includes at least two light emitting diodes: one emitting light at the red wavelength, the other emitting light at the IR wavelength, in response to the control signal from the controller 102. The controller 102 supplies signals to the light source 14 conditioning the light source 14 to produce alternating light signals at the respective wavelengths. Alternately, the controller 102 may condition the LEDs to emit light during mutually exclusive time periods including a time period when no light is emitted by either LED, all in a known manner. The light sensor 16 receives light signals either transmitted through or reflected from the flesh 5. The signals are processed in the appropriate way to produce separate red and IR electrical signals representing the received signals from the corresponding LED in the light source 14, in a known manner. This processing can include noise filtering, dark (no LED light) period processing, gain control, and possibly conversion to digital samples, all in a known manner. In the remainder the diagram, the red and IR electrical signals are represented by single signal lines, unless specifically described otherwise. One skilled in the art will also understand that some of this processing may be performed within the control circuit 100, though such circuitry is not shown in order to simplify the figure.

Because the electrical physiological signals of interest are known to exist only in the frequency band from 0.5 Hz to 5 Hz, the band pass filter 108 filters the received light representative signals and passes only those frequencies within this pass band. The FFT calculating circuit 110 performs a transform of the filtered red and IR signals into the frequency domain. The red and IR FFTs are converted to magnitude transforms by the magnitude calculator 112 in the standard manner. Circuit 114 detects peaks in the magnitude FFT of the IR signal only. Any of the plurality of known methods for detecting peaks may be used on the IR magnitude FFT to detect the peaks.

Figure 2:
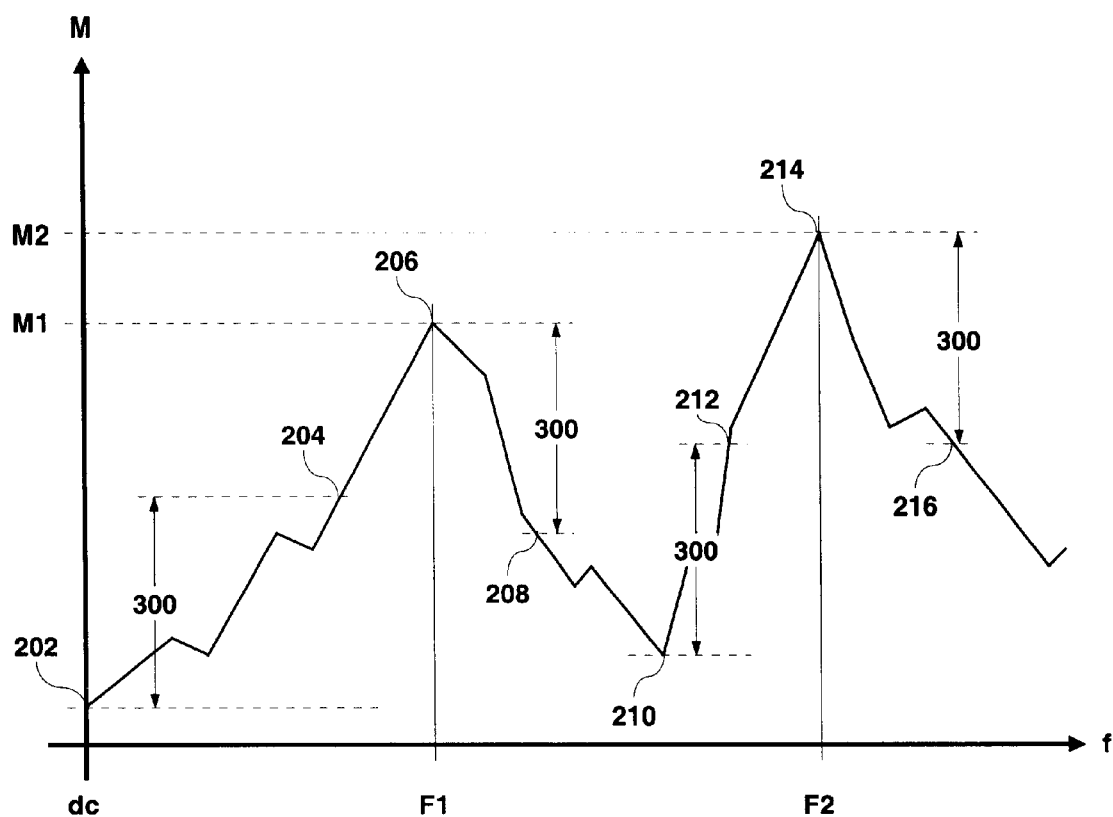
FIG. 2 is a diagram illustrating the method of detecting a spectral peak useful in the system illustrated in FIG. 1.

FIG. 2 is a diagram illustrating the method of detecting a spectral peak useful in the system illustrated in FIG. 1. In FIG. 2, the IR magnitude FFT is traversed from the dc point upward in frequency. A peak is detected whenever the magnitude of the IR FFT rises from a magnitude of the starting point by at least a predetermined amount (e.g. 300) before the magnitude of the IR FFT drops by the predetermined amount below the peak. The detected peak has associated with it a frequency and a magnitude. The frequency of the detected peak is the frequency location in the FFT at which the maximum magnitude is detected, and the maximum magnitude at that frequency location is the peak magnitude.

Referring more specifically to FIG. 2, an exemplary IR magnitude FFT is illustrated. One skilled in the art will understand that such an FFT consists of an ordered set of magnitude values, each value representing the magnitude of the IR signal at a corresponding frequency. However, in order to more clearly describe the method for detecting peak values, this set of values is represented by a line graph representing the magnitude spectrum. Starting at the dc point 202, the magnitude of the IR FFT is monitored to detect when it exceeds the dc value by a predetermined value, which is the illustrated embodiment is 300. In FIG. 2 this occurs at point 204. From point 204, the maximum value of the magnitude of the IR FFT is continually updated, and the magnitude of the IR FFT is monitored to detect when it decreases from the maximum value by the predetermined amount (e.g. 300). More specifically, a maximum is detected at point 206. This maximum has a value of M1 and a frequency of F1. This peak is selected when the magnitude of the IR FFT drops below the maximum magnitude M1 by the predetermined amount (300), which occurs at point 208. From point 208, the minimum value of the magnitude of the IR FFT is continually updated, and the magnitude of the IR FFT is monitored to detect when it increases from the minimum value by the predetermined amount (300). More specifically, a minimum is detected at point 210. This minimum is selected when the magnitude of the IR FFT exceeds the minimum magnitude at point 210 by the predetermined amount (300), which occurs at point 212. The magnitude and frequency of the minimum point are not relevant.

From point 210 the process described above repeats to detect further peaks. Consequently, as described above, from point 212 the maximum value of the magnitude of the IR FFT is continually updated, and the magnitude of the IR FFT is monitored to detect when it decreases from the maximum value by the predetermined amount (300). A second maximum is detected at point 214. This maximum has a value of M2 and a frequency of F2. This peak is selected when the magnitude of the IR FFT drops below the maximum magnitude M2 by the predetermined amount (300), which occurs at point 216. All such peaks are detected in this manner. These peaks are further processed as described below. Alternatively, a predetermined maximum number of peaks may be further processed (e.g. 10 to 30). In this case, the 10 to 30 peaks with the largest magnitudes are further processed, as described below, while the remainder are discarded.

The calculating circuitry 118 calculates in $SpO_2$ value for the frequency of each peak identified by the peak detecting circuitry 114. For each such peak, the calculation is based on the ratio R, given in equation (1) below, in which ACred represents the magnitude of the red FFT at the location of the peak detected in the IR FFT; DCred represents the magnitude of the red FFT at the zero frequency (DC) location; ACir represents the magnitude of the IR FFT at the location of the peak, and DCir represents the magnitude of the IR FFT at the zero frequency (DC) location. The ratio R is then used as an input parameter to an experimentally determined look up table to determine the SpO₂ value corresponding to that ratio.

$$R = \frac{\log\frac{ACred + DCred}{DCred}}{\log\frac{ACir + DCir}{DCir}} \quad (1)$$

Each peak detected by the peak detector 114 is then weighted by weighting circuit 120. The weighting in general is based on the SpO₂ value calculated in the calculating circuitry 118, and other signal features. These signal features may be related to the physiological signals themselves, or to some other signal as illustrated in phantom FIG. 1 by signal lines coupled to a second input terminal of the weighting circuit 120. These signal features could, for example, be a value, slope or integral or some other function of one or more signals, including the physiological signals, in either the time or frequency domain.

In the illustrated embodiment, the weight W is calculated, as illustrated in equation (2) below, by taking the SpO₂ value calculated by the calculating circuit 118, squaring it, and multiplying by the magnitude of the corresponding IR FFT peak (ACir) to produce the weight W corresponding to that peak.

$$W = (SpO_2)^2 \cdot ACir \quad (2)$$

The selection circuitry 122 selects a peak according to a predetermined criterion. In the illustrated embodiment, the peak having the largest weight W is selected as the peak representing the actual pulse rate.

However, if the peak selected the selecting circuitry 122 is between her 0.75 Hz and 1.4 Hz, then it is possible that the frequency of this peak represents not the pulse rate, but instead the first harmonic of the pulse rate and that the spectral peak representing the frequency of the fundamental is masked by noise. Thus, one further check may optionally be performed before the final selection of a peak representing the pulse rate.

Checking circuitry 124 checks the frequency of the peak selected by the selecting circuit 122 to determine if it is between 0.75 Hz and 1.4 Hz. If it is, then the location in the magnitude IR FFT at ½ of the frequency represented by the selected peak is checked to determine if it is has been identified as a peak. If that location is not a peak, then the peak initially selected by the selection circuitry 122 is selected as the peak, and the pulse rate and SpO₂ values corresponding to that peak are produced at the output terminals of the output circuit 126 and displayed on the monitor 128.

On the other hand, if the location of the IR magnitude FFT at ½ of the frequency of the peak initially selected by selecting circuit 122 is determined to also be a peak, then the magnitude of that peak (lower peak) is compared to the magnitude of the peak initially selected by the selecting circuit 122 (upper peak). If the magnitude of the lower peak is greater than twice the magnitude of the upper peak, then the SpO₂ values calculated for the lower and upper peaks are compared. If the SpO₂ value (expressed as a percentage) for the lower peak is more than two percent greater than the SpO₂ value for the upper peak, then the lower peak is assumed to be the fundamental, and the frequency of the lower peak is assumed to represent the pulse rate. In this case the pulse rate and the SpO₂ values corresponding to the lower peak are produced at the output terminals of the output circuit 126 and displayed on the monitor 128. Otherwise, the upper peak is assumed to be the fundamental, and the pulse rate and the SpO₂ values corresponding to the upper peak are produced at the output terminals of the output circuit 126 and displayed on the monitor 128.

The system illustrated in FIG. 1 is described above as consisting of separate interconnected hardware elements, and such a system could be implemented in that manner. However, one skilled in the art will understand that the control circuit 100 could also be implemented as a computer system, operating under control of a control program, in which signals received from the light sensor 16 are converted into samples in digital form by an analog to digital converter in a known manner. The digital samples are received by the computer 100, and all filtering, transforms, and other calculations and comparisons are carried out by the computer under control of a program stored in a memory (not shown) all in a known manner.

By detecting spectral peaks in the electrical red and IR light signals, the amount of calculations which must be performed, relative to the prior art methods, described above, is decreased, and consequently the power required to detect the pulse rate and SpO₂ level is decreased as well.

What is claimed is:

1. A system for detecting a physiological parameter from a physiological signal derived from patient blood, comprising:
   a source of the physiological signal;
   a pre-processor for detecting peaks from an infra-red frequency domain transform representation of a physiological signal;
   a weighting processor for weighting an individual peak of said detected peaks according to at least one of (a) an infra-red frequency domain transform representation value corresponding to said individual peak and (b) a function of a blood oxygen saturation representative value corresponding to said individual peak;
   a peak selector for selecting a weighted peak according to a predetermined criterion; and
   a computational processor for generating a parameter value corresponding to the selected weighted peak.

2. The system of claim 1 further comprising a bandpass filter coupled between the physiological signal source and the pre-processor.

3. The system of claim 1 wherein said weighting processor weights an individual peak of said detected peaks according to at least one of (a) an infra-red frequency domain transform representation value corresponding to said individual peak and (b) a function of a blood oxygen saturation representative value corresponding to said individual peak, and exclusive of other factors.

4. The system of claim 1 wherein said weighting processor weights an individual peak of said detected peaks according to a function of both, (a) the infra-red frequency domain transform representation value corresponding to said individual peak and (b) the blood oxygen saturation representative value corresponding to said individual peak.

5. The system of claim 1 wherein said pre-processor exclusively detects peaks from an infra-red frequency domain transform representation of the physiological signal independently of an associated red light frequency domain transform representation of the physiological signal.

6. The system of claim 1 wherein said infra-red frequency domain transform representation value corresponding to said individual peak comprises at least one of, (a) a value representing a magnitude of the infra-red frequency domain transform corresponding to said individual peak, (b) a value representing an amplitude of the infra-red frequency domain transform corresponding to said individual peak and (c) a peak infra-red frequency domain transform value of said individual peak.

7. The system of claim 1 wherein the weighting processor weights said individual peak according to both the magnitude of the infra-red frequency domain transform corresponding to said individual peak and the blood oxygen saturation representative value corresponding to said individual peak.

8. The system of claim 1 wherein the peak selector selects a weighted peak having the largest weight.

9. A system for deriving a blood oxygen concentration ($SpO_2$) representative value from a physiological signal, comprising:
   a source of the physiological signal;
   a pre-processor for detecting peaks of an infra-red frequency domain transform representation of said physiological signal exclusive of peaks in a red frequency domain transform corresponding to said physiological signal;
   a processor for calculating a blood oxygen concentration representative value corresponding to detected spectral peaks in said infra-red frequency domain transform representation;
   a weighting processor for weighting an individual peak of said detected spectral peaks according to at least one of (a) an infra-red frequency domain transform representation value corresponding to said individual peak and (b) a function of a blood oxygen saturation representative value corresponding to said individual peak;
   a peak selector for selecting a weighted peak having the largest weight; and
   an output processor for providing a blood oxygen concentration representative value corresponding to the selected weighted peak.

10. The system of claim 9 further comprising a bandpass filter coupled between the signal source and the pre-processor.

11. The system of claim 10 wherein the passband of the bandpass filter is substantially between around 0.5 Hz and around 5 Hz.

12. The system of claim 9 wherein the signal source comprises a source of a red signal representing received red light and a source of an infra-red signal representing received infra-red light.

13. The system of claim 12 wherein:
   said pre-processor for detecting peaks of an infra-red frequency domain transform representation of a physiological signal includes a Fourier transform processor which generates transformed red and infra-red signals.

14. The system of claim 13 wherein:
   the Fourier transform processor comprises an FFT circuit.

15. The system of claim 13 wherein the processor for calculating a blood oxygen concentration representative value comprises:
   circuitry for calculating a ratio R value according to the equation:

$$R = \frac{\log \frac{ACred + DCred}{DCred}}{\log \frac{ACir + DCir}{DCir}}$$

wherein ACred represents the magnitude of the transformed red signal at each peak, DCred represents the DC magnitude of transformed red signal, ACir represents the magnitude of the transformed IR signal at each peak, and DCir represents the DC magnitude of the IR signal; and
   a lookup table for looking up the $SpO_2$ value according to the ratio R.

16. The system of claim 13 wherein the weighting processor weights an individual peak of said detected spectral peaks according to the equation:

$$W = (SpO_2)^2 \cdot ACir$$

wherein ACir represents the magnitude of the transformed IR signal at each peak.

17. The system of claim 9 wherein each detected peak is further associated with a frequency, and the system further comprises:
   a processor for determining if the frequency associated with the selected peak is within a predetermined frequency range and if the frequency associated with the selected peak is within the predetermined frequency range, then:
      checking if the transformed signal at one-half the frequency associated with the selected peak is also a peak, and if the signal at one-half the frequency associated with the selected peak is also a peak, then:
         comparing the respective magnitudes associated with the selected peak and the peak at one-half the frequency associated with the selected peak, and if the magnitude of the peak at one-half the frequency associated with the selected peak is greater than the magnitude of the selected peak by a predetermined factor, and the $SpO_2$ value associated with the peak at one-half the frequency associated with the selected peak is greater than the $SpO_2$ value associated with the selected peak by a predetermined amount, then selecting the peak at one-half the frequency of the selected peak.

18. The system of claim 17 wherein the predetermined factor is substantially two.

19. The system of claim 17 wherein the $SpO_2$ value is expressed as a percentage; and the predetermined amount is substantially 2%.

20. The system of claim 17 wherein the predetermined frequency range is from substantially between around 0.5 Hz to around 1.4 Hz.

21. The system of claim 9 comprised in a computer system, operating under control of a control program.

22. A method for detecting a physiological parameter from a physiological signal derived from patient blood, comprising the steps of:
   receiving the physiological signal representing the parameter;
   detecting peaks from an infra-red frequency domain transform representation of the physiological signal;
   weighting an individual peak of said detected peaks according to at least one of (a) an infra-red frequency domain transform representation value corresponding to said individual peak and (b) a function of a blood oxygen saturation representative value corresponding to said individual peak;
   selecting a weighted peak according to a predetermined criterion; and
   generating a physiological parameter corresponding to the selected weighted peak.

23. The method of claim 22 further including the step of limiting the bandwidth of the physiological signal.

24. The method of claim 22 wherein said step of detecting peaks comprises exclusively detecting peaks from an infra-red frequency domain transform representation of the physiological signal independently of an associated red light frequency domain transform representation of the physiological signal.

25. The method of claim 22 wherein said weighting step comprises weighting an individual peak of said detected peaks according to at least one of (a) an infra-red frequency domain transform representation value corresponding to said individual peak and (b) a function of a blood oxygen saturation representative value corresponding to said individual peak, and exclusive of other factors.

26. The method of claim 22 wherein said infra-red frequency domain transform representation value corresponding to said individual peak comprises at least one of, (a) a value representing a magnitude of the infra-red frequency domain transform corresponding to said individual peak, (b) a value representing an amplitude of the infra-red frequency domain transform corresponding to said individual peak and (c) a peak infra-red frequency domain transform value of said individual peak.

27. The method of claim 26 wherein the weighting step comprises the step of weighting said individual peak according to both the magnitude of the infrared frequency domain transform corresponding to said individual peak and the blood oxygen saturation representation value corresponding to said individual peak.

28. The method of claim 22 wherein the selecting step comprises the step of selecting a weighted peak having the largest weight.

29. A method for detecting blood oxygen concentration (SpO$_2$) representative value from a physiological signal, comprising the steps of:

receiving the physiological signal representing the SpO$_2$ value;

detecting peaks of an infra-red frequency domain transform representation of said physiological signal exclusive of peaks in a red frequency domain transform corresponding to said physiological signal;

calculating the SpO$_2$ representative value corresponding to detected spectral peaks;

weighting an individual peak of said detected spectral peaks according to at least one of (a) an infra-red frequency domain transform representation value corresponding to said individual peak and (b) a function of a blood oxygen saturation representative value corresponding to said individual peak;

selecting a weighted peak with the highest weight; and generating the SpO$_2$ representative value corresponding to the selected weighted peak.

30. The method of claim 29 further including the step of limiting the bandwidth of the physiological signal.

31. The method of claim 30 wherein the limiting step comprises the step of limiting the bandwidth to substantially between around 0.5 Hz to around 5 Hz.

32. The method of claim 29 further including a transforming step comprising the step of transforming the red and IR signals to transformed red and IR signals, respectively; and wherein the receiving step comprises the step of receiving a red signal representing received red light and an IR signal representing received IR light;

wherein the detecting step comprises the step of detecting peaks in the transformed IR signal.

33. The method of claim 32 wherein the transformed physiological signal has a DC magnitude, and the calculating step comprises the steps of:

calculating a ratio R value according to the equation:

$$R = \frac{\log \frac{ACred + DCred}{DCred}}{\log \frac{ACir + DCir}{DCir}}$$

wherein ACred represents the magnitude of the transformed red signal at each peak, DCred represents the DC magnitude of transformed red signal, ACir represents the magnitude of the transformed IR signal at each peak, and DCir represents the DC magnitude of the IR signal; and looking up the SpO$_2$ representative value from a lookup table according to the ratio R.

34. The method of claim 32 wherein the weighting step comprises the step of weighting an individual peak of said detected spectral peak according to the equation:

$$W = (SpO_2)^2 \cdot ACir$$

wherein ACir represents the magnitude of the transformed IR signal at peak.

35. The method of claim 32 wherein the transforming step further comprises the step of transforming the red and IR signals to magnitude transformed red and IR signals, respectively.

36. The method of claim 29 wherein each detected peak is further associated with a frequency, and the method further comprises, after the selecting step, the steps of:

determining if the frequency associated with the selected peak is within a predetermined frequency range and if the frequency associated with the selected peak is within the predetermined frequency range, then performing the steps of:

checking if the transformed signal at one-half the frequency associated with the selected peak is also a peak and if the signal at one-half the frequency associated with the selected peak is also a peak, then performing the steps of:

comparing the respective magnitudes associated with the selected peak and the peak at one-half the frequency associated with the selected peak; and if the magnitude of the peak at one-half the frequency associated with the selected peak is greater than a predetermined factor times the magnitude of the selected peak, and the SpO$_2$ value associated with the peak at one-half the frequency associated with the selected peak is greater than the SpO$_2$ value associated with the selected peak by a predetermined amount, then selecting the peak at one-half the frequency of the selected peak.

37. The method of claim 36 wherein the predetermined factor is substantially two.

38. The method of claim 36 wherein the SpO$_2$ representative value is expressed as a percentage; and the predetermined amount is substantially 2%.

39. The method of claim 36 wherein the predetermined frequency range is from substantially between about 0.5 Hz to about 1.4 Hz.

* * * * *